(12) United States Patent
Van Dreden et al.

(10) Patent No.: US 8,647,833 B2
(45) Date of Patent: Feb. 11, 2014

(54) METHOD FOR IN VITRO ASSAY OF THE CIRCULATING TISSUE FACTOR, AND USE IN THE DETECTION OF COAGULATION DISEASES

(75) Inventors: Patrick Van Dreden, Brennilis (FR); Aurelie Rousseau, Louveciennes (FR); Barry Woodhams, Le Plessis Bouchard (FR)

(73) Assignee: Diagnostica Stago, Asnieres (FR)

( * ) Notice: Subject to any disclaimer, the term of this patent is extended or adjusted under 35 U.S.C. 154(b) by 554 days.

(21) Appl. No.: 13/054,578

(22) PCT Filed: Jul. 16, 2009

(86) PCT No.: PCT/EP2009/059182

§ 371 (c)(1),
(2), (4) Date: Jan. 18, 2011

(87) PCT Pub. No.: WO2010/007140

PCT Pub. Date: Jan. 21, 2010

(65) Prior Publication Data

US 2011/0250621 A1    Oct. 13, 2011

(30) Foreign Application Priority Data

Jul. 17, 2008   (FR) ..................... 08 04073

(51) Int. Cl.
*G01N 31/00*   (2006.01)
*G01N 33/53*   (2006.01)

(52) U.S. Cl.
USPC ........... 435/7.21; 435/7.1; 436/501; 436/518; 424/9.1; 422/430; 530/300; 530/350

(58) Field of Classification Search
None
See application file for complete search history.

(56) References Cited

U.S. PATENT DOCUMENTS 5,705,396 A    1/1998   Fickenscher et al.

FOREIGN PATENT DOCUMENTS

EP    1367135 A    3/2003
WO    2006096345 A    9/2006

OTHER PUBLICATIONS

Bendz B et al: "A new sensitive chromogenic substrate assay of tissue factor pathway inhibitor type 1", Thrombosis Research Mar. 15, 2000, vol. 97, No. 6, Mar. 15, 2000, pp. 463-472, XP002505261.
Fukuda C et al: "Measuring tissue factor (factor III) activity in plasma." Clinical Chemistry Sep. 1989, vol. 35, No. 9, Sep. 1989, pp. 1897-1900, XP002505262.
Hische E A et al: "Spectrophotometry of tissue thromboplastin in cerebrospinal fluid." Clinical Chemistry Aug. 1981, vol. 27, No. 8, Aug. 1981, pp. 1427-1430, XP002505263.
Bladbjerg E M et al: "In vitro effects of heparin and tissue factor pathway inhibitor on factor VII assays. possible implications for measurements in vivo after heparin therapy" Blood Coagulation &Fibrinolysis, Rapid Communications, Oxford,Oxford, GB, vol. 11, No. 8, Dec. 1, 2000, pp. 739-745, XP009069876.
Database Biosis Biosciences Information Service, Philadelphia, PA, US; Nov. 2004, Smith Stephanie A et al: "Do elevated plasma tissue factor pathway inhibitor (TFPI) levels affect measurement of factor VIIa?" XP002505264.
Database Medline US National Library of Medicine (NLM), Bethesda, MD, US; Feb. 1995, Murakami Fetal: "[An improved assay for plasma tissue factor activity]" XP002505265.
Krupinski Jerzy et al: "Blood-borne tissue factor activity predicts major cerebrovascular events in patients undergoing carotid endarterectomy: results from a I-year follow-up study." Cerebrovascular Diseases (Basel, Switzerland) 2008, vol. 25, No. 1-2, Nov. 22, 2007, pp. 32-39, XP008098991.
Eilertsen K-E et al: "Tissue Factor: (Patho)Physiology and Cellular Biology" Blood Coagulation &Fibrinolysis, Rapid Communications, Oxford,Oxford, GB, vol. 15, No. 7, Jan. 1, 2004, pp. 521-538, XP008065964.
International Search Report, dated Aug. 26, 2009, in PCT/EP2009/059182.
French Search Report, dated Nov. 27, 2008, in Application No. FA 710318/FR0804073.

*Primary Examiner* — Lisa Cook
(74) *Attorney, Agent, or Firm* — Young & Thompson

(57) ABSTRACT

The invention concerns the field of hemostasis, in particular blood coagulation disorders linked to an abnormal expression of tissue factor, and to physiopathological phenomena correlated with over-expression of the factor. The present invention provides a method for assaying the activity of circulating tissue factor in a biological sample. The method of the invention is carried out in vitro, in particular on a blood sample collected from a patient.

25 Claims, 10 Drawing Sheets

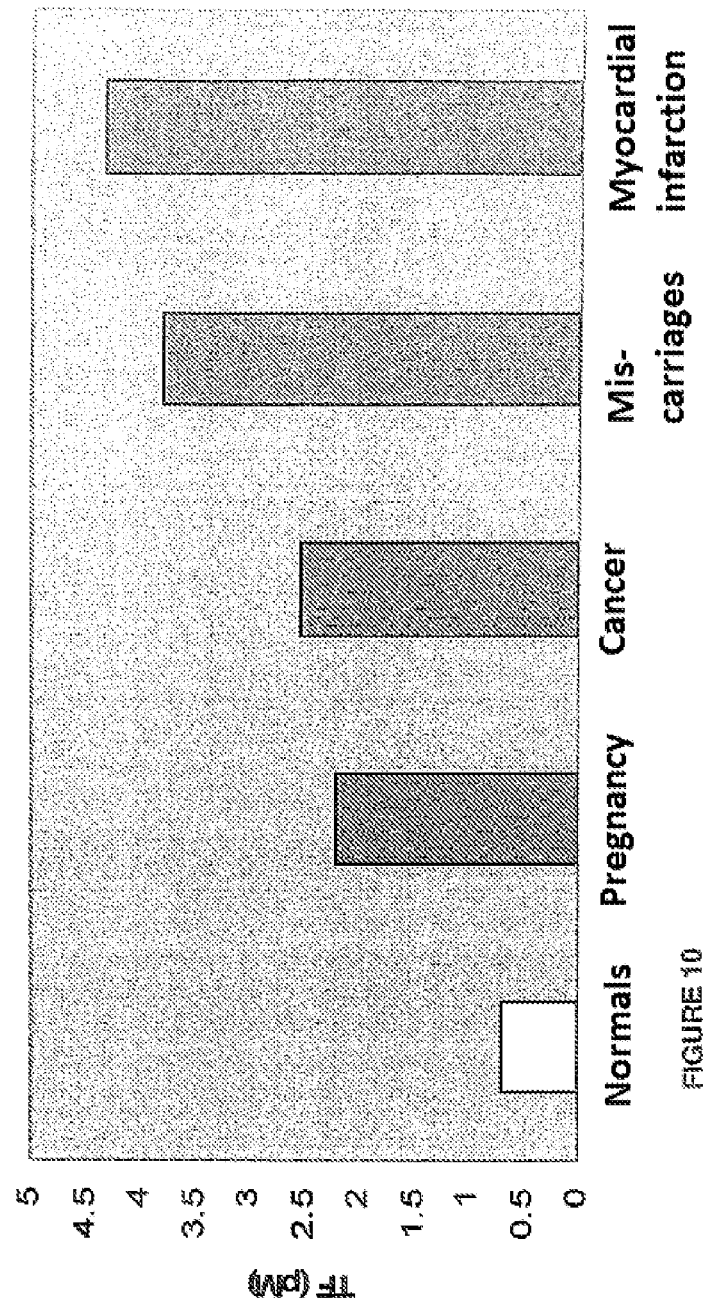

Figure 1:
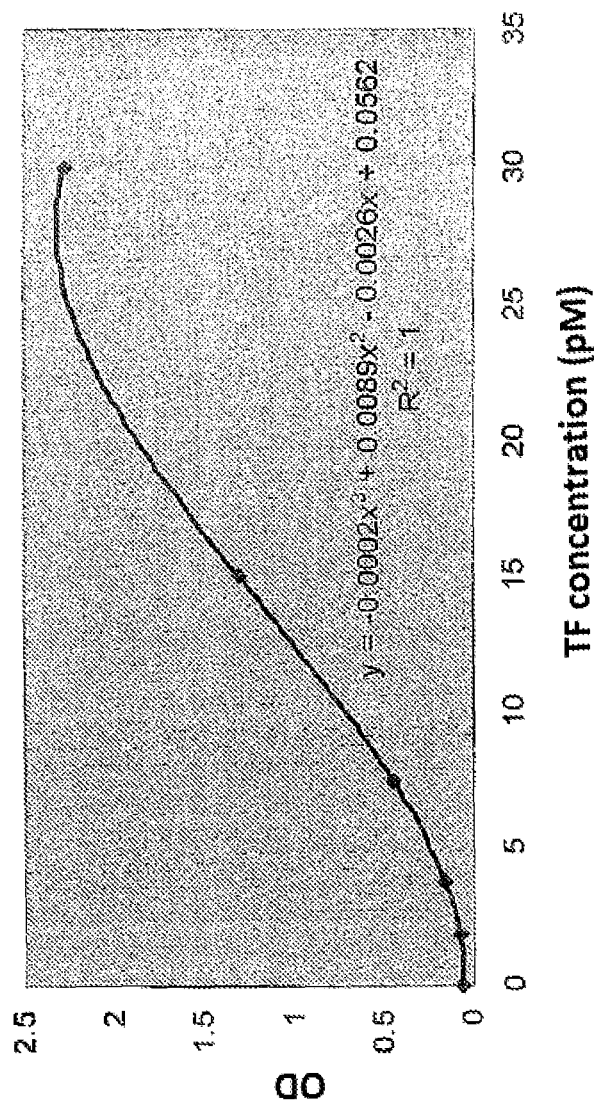
Figure 2:
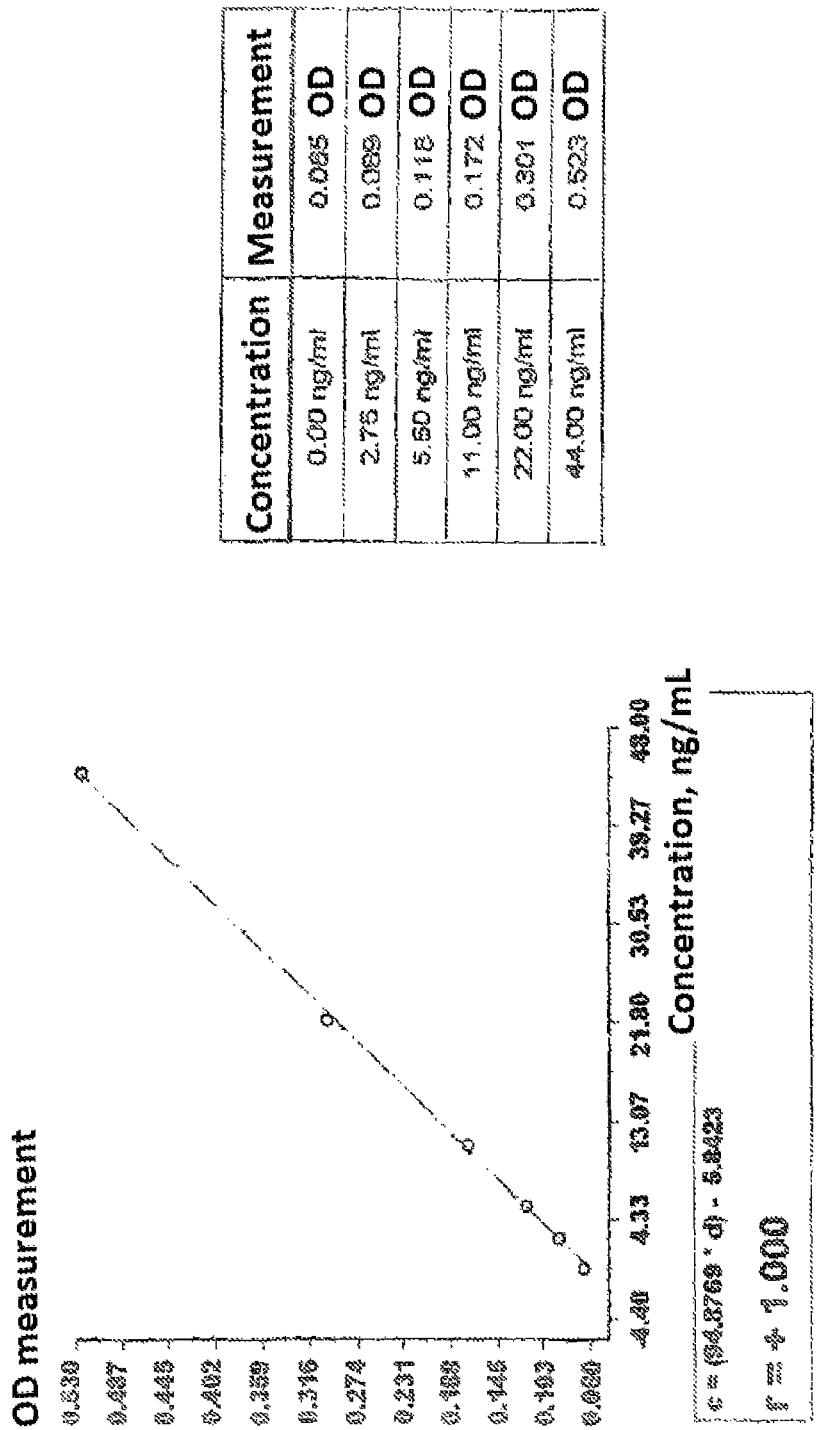

SEQUENCE LISTING

<160> NUMBER OF SEQ ID NOS: 1

<210> SEQ ID NO 1
<211> LENGTH: 4
<212> TYPE: PRT
<213> ORGANISM: Artificial Sequence
<220> FEATURE:
<223> OTHER INFORMATION: Synthetic Oligopeptide

<400> SEQUENCE: 1

Gly Pro Arg Pro
1

METHOD FOR IN VITRO ASSAY OF THE CIRCULATING TISSUE FACTOR, AND USE IN THE DETECTION OF COAGULATION DISEASES

The invention relates to the field of hemostasis, in particular blood coagulation disorders linked to abnormal expression of tissue factor, and to physiopathological phenomena correlated with overexpression of that factor.

The present invention pertains to a method for assaying the activity of circulating tissue factor in a biological sample.

The method of the invention is carried out in vitro, in particular on a blood sample taken from a patient, or on a sample prepared from a blood sample that has been taken.

The method of the invention is preferably carried out in a plasma medium. Advantageously, it employs a chromogenic type assay.

Tissue factor, the principal activator in in vivo coagulation, is a 47 kDa transmembrane glycoprotein which binds with factor VII or VIIa to form the tissue factor-factor VIIa complex which, by activation of factors IX and X, triggers coagulation activation, entraining the generation of thrombin and the formation of fibrin. Indeed coagulation initiation requires factor VII to bind to its specific surface protein receptor, tissue factor, expressed by a certain number of cells or by their components (endothelium, monocyte-macrophages, smooth muscle cells, fibroblasts, epitheliums, microparticles of cellular origin, platelets after molecular transfer from microparticles of monocytary origin, neoplasic cells). The activity of the tissue factor-VIIa complex is involved not only in normal hemostasis but also in the onset of thromboses associated with malignant diseases, acute coronary syndromes and severe sepsis. Regulation of this essential activity in maintaining hemostatic equilibrium is ensured by a tissue factor pathway inhibitor, TFPI (tissue factor pathway inhibitor). This inhibitor, TFPI, does not inactivate tissue factor, but rather the catalytic activity of the tissue factor-factor VIIa complex. First, TFPI binds to factor Xa, and factor Xa is then inhibited; secondly, the Xa/TFPI complex can bind to the factor VIIa-tissue factor complex to form a quaternary factor Xa/TFPI/factor VIIa/tissue factor complex within which the factor Xa, the factor VIIa and the tissue factor no longer have activity. Thus, TFPI limits the activation of coagulation induced by the expression of Tissue Factor (TF), imposing a kind of initial stage to surmount before the initial molecular events of coagulation can actually induce activation of the coagulation cascade. Thus, TFPI allows a low noise exposure of tissue factor, with no pro-coagulation consequences. TFPI is synthesized by endothelial cells and platelets.

Under physiological conditions, the expression of tissue factor is ubiquitous and it is present on the surface of a wide variety of cell types, with the exception of cells in direct contact with circulating blood (endothelial cells and figurative blood elements). The adventitia of the vessels, the myocardium, the mucous tissues and epidermal tissues are very rich in tissue factor.

Thrombosis on atherosclerotic plaques, which are responsible for acute ischemic arterial events, are closely linked to pathological exposure to tissue factor. The thrombogenicity of atherosclerotic plaques is correlated to the quantity of tissue factor present, which considerably reinforces the thrombogenicity process in the case of plaque rupture. Similarly, during sepsis, tissue factor can be expressed by monocytes and endothelial cells and be responsible for disseminated intravascular coagulation. Tissue factor has also been identified on the surface of microparticles derived from cell membranes. Such microparticles, originating from monocytes and lymphocytes, have been identified in atherosclerotic plaques. They have procoagulating activity and are derived from apoptopic cells.

In addition to its procoagulating activity, tissue factor is currently considered to be a protein having functions comparable to those of a hormone on various cell populations (1).

Hence, for example, it has been shown that tissue factor enhances the production of vascular endothelial growth factor (VEGF) and induces in vivo and in vitro angiogenesis.

Tissue factor also stimulates cell migration, and its involvement in metastases and in the organization and integrity of the wall of vessels in angiogenesis associated with tumors has already been described (2).

Thus, it is now clear that tissue factor is involved in a variety of physiopathological situations, and for this reason it is necessary to have available an assay method that can follow variations in its activity not only in thrombotic risk situations but also in monitoring the evolution of certain pathologies, especially cancers.

Conventional methods for assaying blood or plasmatic tissue factor are methods of an immunological type, such as ELISA type methods, which measure only the antigen and thus are quantitative rather than qualitative assays.

Various activity tests have been illustrated in the literature, the majority being carried out starting from cell extracts using a chronometric method (measuring the time for a clot to form) using the principle described in (3).

Other TF activity tests consist of evaluating the generation of activated factor X (FXa) in the presence of activated factor VII (FVIIa) and calcium and a specific substrate for factor Xa.

The test thus consists of measuring the capacity of the TF-FVIIa complex to activate FX to FXa.

This activation of FX may be calculated from the quantity of hydrolyzed substrate, for example using a chromogenic method, when a substrate is used which generates a chromogenic group upon hydrolysis.

The majority of tests for activity based on that scheme are made on plasma samples that have been defibrinated, i.e. treated so as to prevent polymerization of fibrin monomers, which would perturb the optical measurements made when carrying out the tests. However, this prior step complicates automation of this type of test and necessitates carrying out the test in two stages.

Further, prior art activity tests do not take into account variations in the quantity of TFPI in the plasma, which could distort the actual activity of the measured TF, and thus provide incorrect information regarding the thrombogenic potential of a patient linked to its TF count.

The present invention is aimed at deviating from the problems encountered in prior art tests.

To this end, it proposes a method for a single step assay of the activity of circulating tissue factor, in which the inhibiting effect of TFPI on tissue factor is neutralized.

Indeed, the invention consist in carrying out in vitro assay of the activity of circulating tissue factor in a biological sample in the presence of a fibrin polymerization inhibitor and a compound inhibiting the action of TFPI on tissue factor.

More precisely, the method of the invention allows the measurement of the factor Xa generated by the activity of circulating tissue factor when an excess of coagulation factors VII and X is added to the reaction medium formed by the test biological sample, the fibrin polymerization inhibitor and the inhibitor of the action of TFPI on TF.

The present invention also pertains to a method for single step in vitro assay, in a biological sample, of the activity of circulating tissue factor, said method being based on the capacity of circulating tissue factor to generate factor Xa in the presence of an excess of factors VII and X.

The biological sample on which the method of the invention is carried out is a sample originating from the sampling of an individual.

It is preferably a blood sample, and more preferably a plasma sample.

However, the method of the invention may also be carried out on a urine sample or cerebrospinal fluid (CSF), or other biological samples.

The method of the invention is preferably an enzymatic type method in which the quantity of Xa formed is determined by measurement of the hydrolyzing activity of this factor on a specific substrate.

In particular, said substrate is an enzymatic substrate, natural or synthetic. It is preferably a substrate that can assay the amidolytic activity of factor Xa. In particular, it is a chromogenic or fluorogenic substrate.

Such a substrate, of the chromogenic type, is, for example, CBS 5244 from Diagnostica Stago (other possible suppliers: American Diagnostica; Biopep SA; Kabi Vitrum; Biogenic; Biophen; Chromogenix).

The quantity of factor Xa generated (and thus the measurement of the activity of circulating tissue factor) is calculated from an assay of the quantity of hydrolyzed substrate.

Said assay may be carried out by measuring the variation in the optical density of the reaction mixture in a reading window that is determined in accordance to the selected substrate.

In one particular implementation of the invention, the plasma obtained from the biological sample removed from the patient is diluted in a suitable buffer.

It may, for example, be Owren Koller buffer, which is frequently used in hemostasis tests.

The dilution obtained depends on the nature of the test sample and on the sensitivity of the substrate used.

In the case of a plasma sample, it is advantageously in the range 1/2 to 1/20, preferably in the range 1/2 to 1/4.

The calcium ions are, for example, supplied in the form of $CaCl_2$.

The fibrin polymerization inhibitor is selected from compounds that are routinely used in the art.

In particular, it is a polypeptide inhibitor, such as the oligopepetide GPRP.AcOH (SEQ ID NO: 1) known under the trade name Pefabloc and supplied by Pentapharm.

That inhibitor may be used in the reaction medium in a concentration of 5 to 25 g/L, selected in accordance to the dilution of the test plasma. As an example, when the plasma is diluted by 1/3, that inhibitor is advantageously used in a concentration of 10 g/L, i.e. a final concentration in the range of 0.666 g/L to 3.33 g/L, in particular 1.332 g/L.

Although Pefabloc constitutes a preferred fibrin polymerization inhibitor for the method of the invention, it is also possible to use inhibitors of another type such as anti-fibrinogen antibodies, for example.

TFPI inhibitor is a compound that inhibits the inhibiting effects of TFPI on circulating TF, thus allowing a quantitative assay of TF that is not distorted by variations in the level of TFPI present in the sample.

The TFPI inhibitor is selected from any type of compound with a TFPI antagonist effect. It is preferably anti-TFPI antibody or antibody fragments binding TFPI, said antibodies possibly being monoclonal, polyclonal or single chain.

In accordance with a particular implementation of the invention, the antibody T4E2 is used, which is a monoclonal antibody supplied by Diagnostica Stago.

Its concentration is selected so as to inhibit all of the TFPI contained in the test sample. It can vary as a function of the study sample, from 5 to 500 µg/mL (concentration in the dilution buffer). In the case of a plasma sample diluted by 1/3, the final antibody concentration is preferably 6.6 µg/mL.

In accordance with the method of the invention, the reaction medium advantageously comprises an excess of factors VII and X. These factors can be used to measure the activity of tissue factor since, as it was explained above, tissue factor binds to activated factor VII (FVIIa) to form a complex which will then activate factors IX and X. Since the activity of TF is measured via the quantity of factor Xa produced, because the hydrolysis of a specific substrate for Xa is measured, then factors VII and X must not limit the reaction so that the quantity of Xa produced is directly correlated to the activity of TF.

Thus, these factors are added in excess, which means that the risk of their interfering in the measurement is avoided.

Depending on the type of sample tested, the final concentrations of each of these two factors are advantageously in the range 5 to 20 PEU/mg/mL for factor VII and in the range 3 to 16 PEU/mg/mL for factor X.

In accordance with a particular implementation of the invention, factor VII is in a concentration of 137 PEU/mg/mL and factor X is in a concentration of 80 PEU/mg/mL when the sample is a plasma diluted by 1/3 (PEU=plasma equivalent unit).

These factors may be purified or recombinant, of human or animal origin. They are, for example, supplied by Diagnostica Stago, Enzyme Research Laboratories, or Sigma.

In a preferred variant embodiment, the tested plasma sample also contains a heparin inhibitor compound, so as to render the test independent of heparin that may be present in the plasma, for example in the context of the assay of a sample from a patient undergoing heparin treatment.

This compound is for example polybrene, conventionally used to inhibit the effects of heparin in hemostasis tests.

It is advantageously used in a final concentration range in the range 0.5 to 10 mg/L.

The skilled person will be capable of adapting the concentrations and activities in accordance to the selected reagents.

By way of illustration, it should be noted that the concentrations or activities of the reagents may vary by an amount of plus or minus 50%, for example plus or minus 20%, or even by plus or minus 10% with respect to the indications contained in the present application. This variation may concern each reagent, independently of the other reagents.

In accordance with a particular implementation, the method of the invention is carried out using the following protocol:

The measurement was carried out using an automated apparatus from the STA range supplied by Diagnostica Stago.

A plasma sample was diluted by 1/3 in a dilution buffer composed of Owren Koller buffer supplemented with 12 mg/L of polybrene and 50 µg/L of anti-TFPI antibody (T4E2).

The following was added to 50 µl of this mixture:
25 µl of a solution comprising 80 PEU/mg/mL of factor X (lyophilized flask taken up in purified water: final concentration 8 PEU/mg/mL);
25 µl of a solution comprising 137 PEU/mg/mL of factor VII (lyophilized flask taken up in purified water: final concentration 13.7 PEU/mg/mL);
50 µl of a 25 mM $CaCl_2$ solution.

This reaction medium was incubated at 37° C. for 500 seconds.

After the incubation step, 100 µl of a solution comprising the CBS 5244 substrate in a concentration of 0.84 µM was added to give a final concentration of 3.36 µM (flask taken up with purified water).

Figure 3:
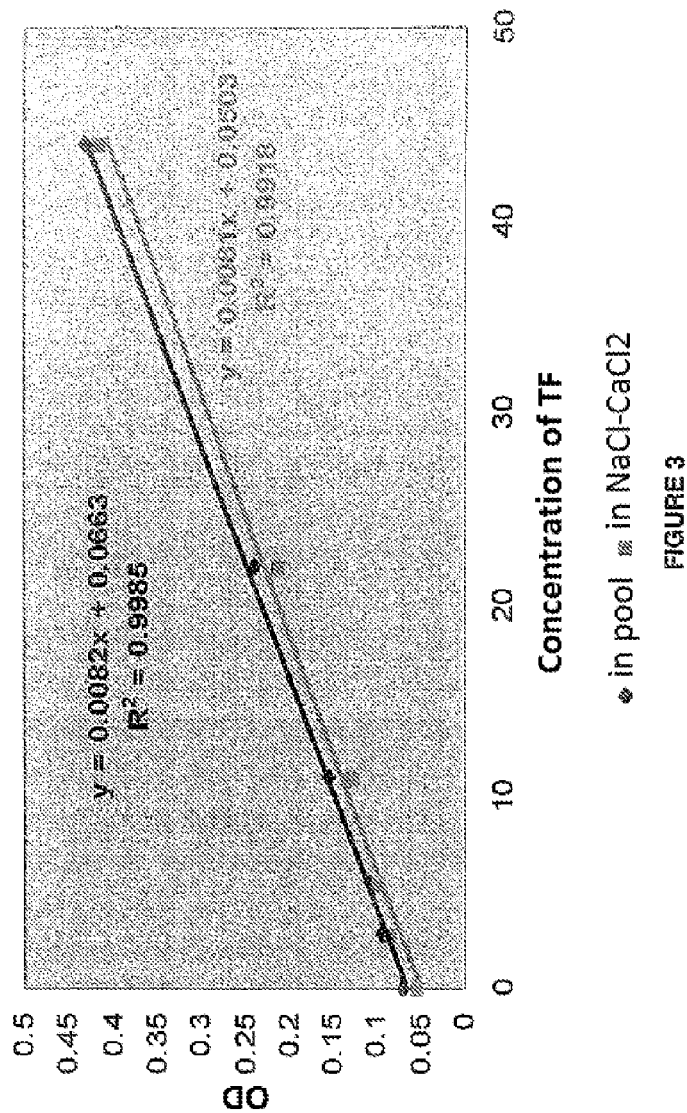

In order to construct the calibration curve, giving the functional activity of tissue factor, the following were used:
either a normal plasma pool enriched in tissue factor: for example, by enriching a pool with 0.00 to 44 pM of TF (FIG. 3);
or a NaCl—CaCl$_2$ solution enriched in tissue factor (FIG. 3).

Each dilution of plasma was tested at a dilution of 1/3.

The concentration of TF added to the plasma pool corresponding to an activity of 44 pM, 22 pM, 11 pM, 5.50 pM, 2.75 pM and 0 pM was determined.

The tissue factor activity was determined on a synthetic substrate for factor Xa, CBS 52.44. In fact, in the presence of FVII, TF will activate FX to FXa. The amidolytic activity of FXa was measured by the liberation of para-nitroaniline at a wavelength of 405 nm. The optical density that corresponded to each value (in pM) of the tissue factor activity was determined in a reading window of 6 to 600 seconds at a wavelength of 405 nm.

Figure 4:
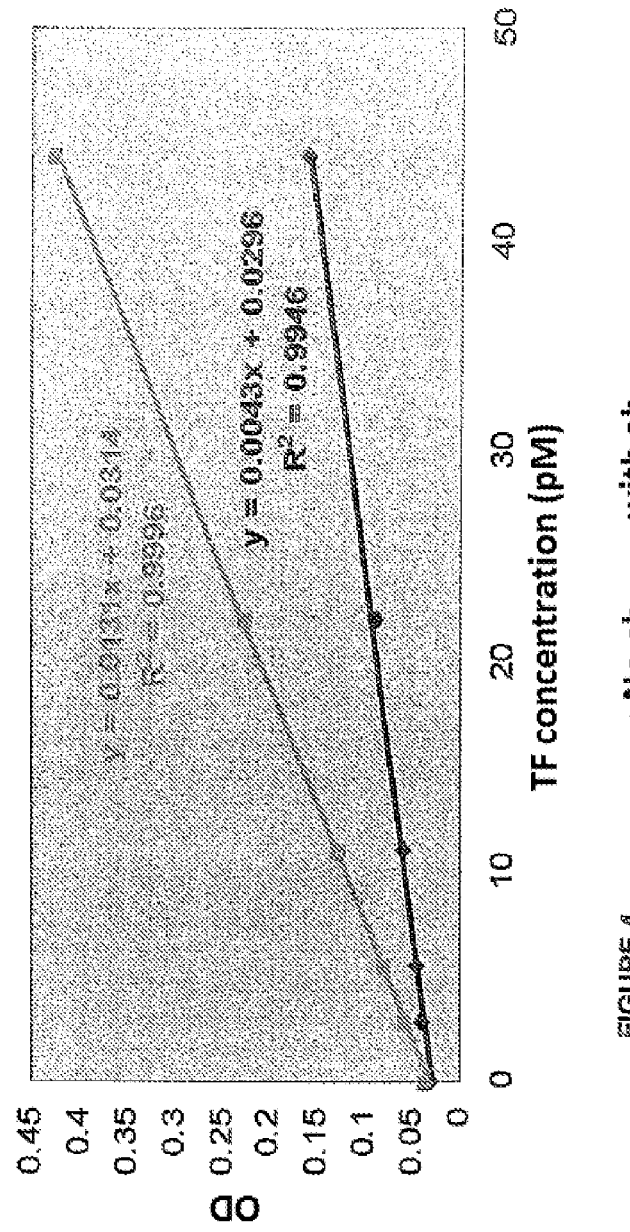

The effect of anti-TFPI antibodies on the calibration was then measured (FIG. 4 and Table 1).

TABLE 1

| Calibration (1) ± anti-TFPI antibody | | | | | | |
|---|---|---|---|---|---|---|
| | TF (pM) | | | | | |
| | 44 | 22 | 11 | 5.5 | 2.75 | 0 |
| No antibody | 0.161 | 0.088 | 0.059 | 0.046 | 0.041 | 0.031 |
| With antibody | 0.427 | 0.224 | 0.127 | 0.080 | 0.057 | 0.035 |

The invention also pertains to a kit for measuring the activity of circulating tissue factor, in particular in a plasma sample, comprising:
a reagent 1 comprising a dilution buffer for the tested sample, a fibrin polymerization inhibitor, a TFPI inhibitor and, if appropriate, a heparin inhibitor;
purified or recombinant factor VII, advantageously lyophilized;
purified or recombinant factor X, advantageously lyophilized;
calcium ions, for example in the form of CaCl$_2$;
an enzymatic substrate for activated factor X, advantageously lyophilized;
if appropriate, a calibration agent, advantageously lyophilized.

The invention also pertains to a method for in vitro detection of a blood coagulation anomaly, comprising measuring the activity of circulating tissue factor as described in the present application. The measurement may be carried out in the context of various physiopathological situations.

In particular, it may concern determining the thrombogenic potential of a patient who is susceptible of developing a thrombosis, and thus subject to an abnormal release of tissue factor resulting in an increased activity of said factor with respect to factor X.

Further, various studies have been carried out to evaluate the role of several hemostatic markers during pregnancy, in order to differentiate preeclampsia situations from normal pregnancies.

As reported in the examples below, it appears that tissue factor activity measured in the plasma from women with preeclampsia is higher than that measured in women with a normal pregnancy and in women who are not pregnant.

Thus, tissue factor may constitute a novel biological marker for evaluating the damages suffered by the vascular endothelium in the case of preeclampsia.

The invention thus advantageously provides a method for evaluating the risk of a preeclampsia situation in the case of pregnancy, in which the circulating TF activity is measured in accordance with the invention. The invention also provides a kit for carrying out said method.

Similarly, as also indicated in the examples below, the TF activity assay, and in particular the activated TF/free TFPI ratio, provides a novel tool for monitoring the evolution of pathologies, for example in order to monitor an acute myocardial infarction (AMI), in which disease both the activated TF count and the activated TF/free TFPI ratio are increased compared with controls, and to establish a favorable or unfavorable prognosis with respect to of the evolution of this pathology.

Thus, the invention offers a method for monitoring or establishing a prognosis for an acute myocardial infarction in which the circulating TF activity or the circulating TF/free TFPI ratio is measured in accordance with the invention. The invention also provides a kit for carrying out said method.

Finally, as demonstrated in recent data presented, for example, in international meetings (ASH Meeting, Atlanta USA, 7-11 Dec. 2007, Thrombosis and Haematosis Issues in Cancer, Bergame, Italy 26-28 Oct. 2007), the involvement of tissue factor in the appearance and development of cancers is now well recognized. On the diagnostic level, assaying the activity of TF, especially an increase therein, is a novel indicator for monitoring the evolution of cancerous pathologies.

Thus, the invention advantageously offers a method for monitoring the evolution of cancerous pathologies, in which the circulating TF activity is measured in accordance with the invention. The invention also provides a kit for carrying out said method.

Thus, assaying tissue factor activity could be of advantage in evaluation and prognosis of various pathologies associated with pregnancy, in particular in order to evaluate the risks of miscarriage and pregnancy complications such as preeclampsia, thrombosis, sepsis, cancers, inflammations, DIVC, diabetes, thrombopenias, and also said assay may be of interest in evaluating anti-thrombotic treatments such as TFPI treatments, for example.

The figures and examples below illustrate the present invention.

With the aim of estimating the normal value for a plasma, 31 normal plasmas were assayed for tissue factor activity using the method of the invention. The measurements of optical density and corresponding TF activity percentages are reported in the table below. Said measurements may be considered to be indicators of normal values of functional activity of tissue factor in normal plasmas.

| | Normal plasmas | |
|---|---|---|
| | Normal plasmas n = 31 | |
| | OD | pM |
| Mean | 0.038 | 0.79 |
| Median | 0.037 | 0.72 |

-continued

Normal plasmas

| | Normal plasmas n = 31 | |
|---|---|---|
| | OD | pM |
| Min | 0.025 | <0.10 |
| MXa | 0.055 | 1.15 |

The sensitivity to heparin was evaluated by adding increasing concentrations of calciparine (0-2 IU/mL) to a plasma enriched in TF (22 pM) assayed under the assay conditions described above. The insensitivity test to heparin exhibited recovery rates >94% (Table 2). This shows that calciparine is of low determinancy for the functional activity of TF.

TABLE 2

Sensitivity to heparin
The sensitivity study was carried out on a range
of calciparine in pool + TF 22 pM

| | OD | pM | Recovery |
|---|---|---|---|
| Pool – TF 22 pM | 0.207 | 22 | 100% |
| Calciparine 0.4 | 0.189 | 20.6 | 94% |
| Calciparine 1.0 | 0.199 | 22 | 100% |
| Calciparine 1.4 | 0.204 | 22 | 100% |
| Calciparine 2.0 | 0.203 | 22 | 100% |

Plasmas enriched in TF comprising a predetermined varying concentration of factor VII were assayed using the method described above.

They were:
plasma deficient in factor VII (0% column);
plasma from a pool rendered more or less deficient in factor VII (25-87.5% columns);
plasma from a normal pool (100% column).

Figure 5:
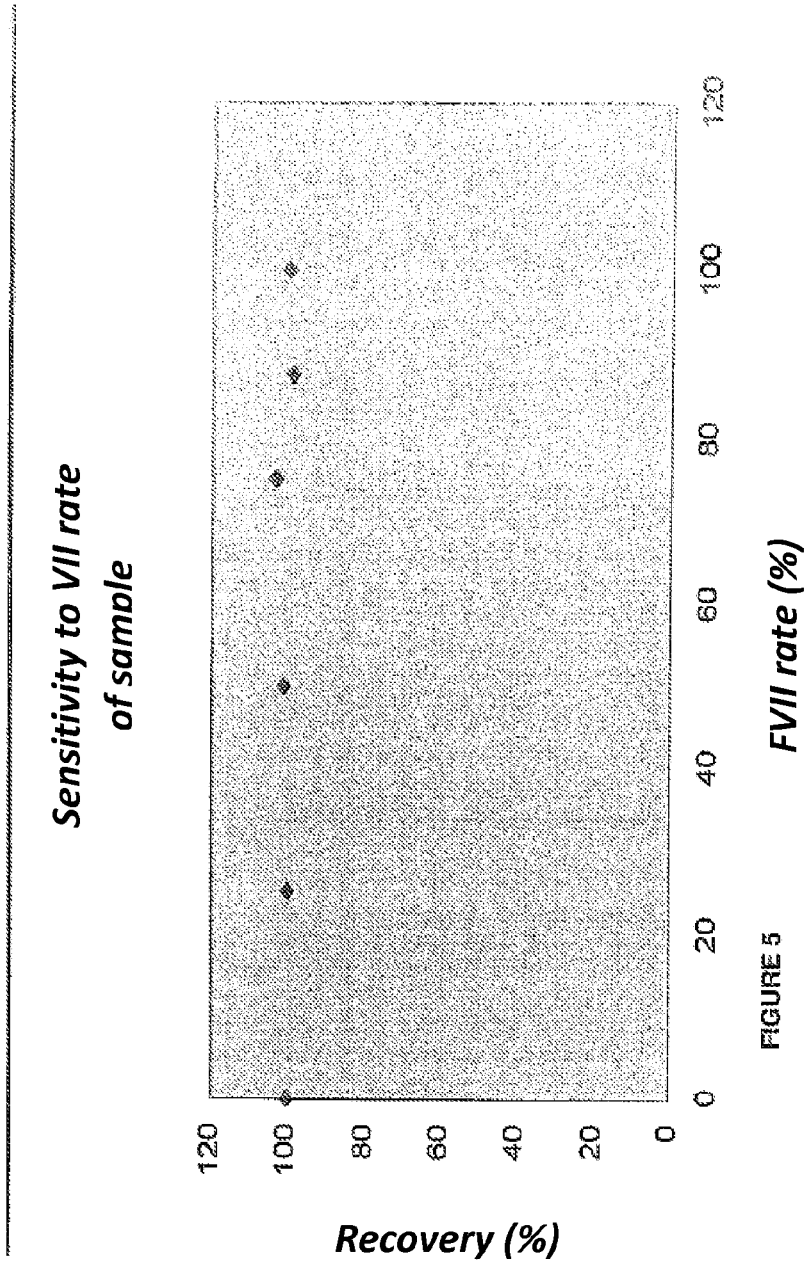

The results (FIG. 5 and Table 3) show, with recovery rates ≥99%, that the factor VII rate in the sample does not influence the value of the functional activity of TF.

TABLE 3

Sensitivity to factor VII (1)

| | VII rate, % | | | | | |
|---|---|---|---|---|---|---|
| | 0 | 25 | 50 | 75 | 87.5 | 100 |
| Theoretical rate TF (pM) | 39.97 | 40.66 | 41.36 | 42.05 | 42.41 | 42.76 |
| Measured rate TF (pM) | 39.97 | 40.66 | 41.88 | 43.58 | 42.07 | 42.76 |
| Recovery % | 100 | 100 | 101 | 104 | 99 | 100 |

Sensitivity carried out from a VII-deficient and from a tissue factor-enriched pool.
0: def VII-TF-pool
25-87.5%: TF-pool/def VII-TF
100%: TF-pool Plasmas enriched in TF containing a predetermined varying concentration of factor X were assayed using the method described above.

They were:
plasma deficient in factor X (0% column);
plasma from a pool rendered more or less deficient in factor X (25-87.5% columns);
plasma from a normal pool (100% column).

Figure 6:
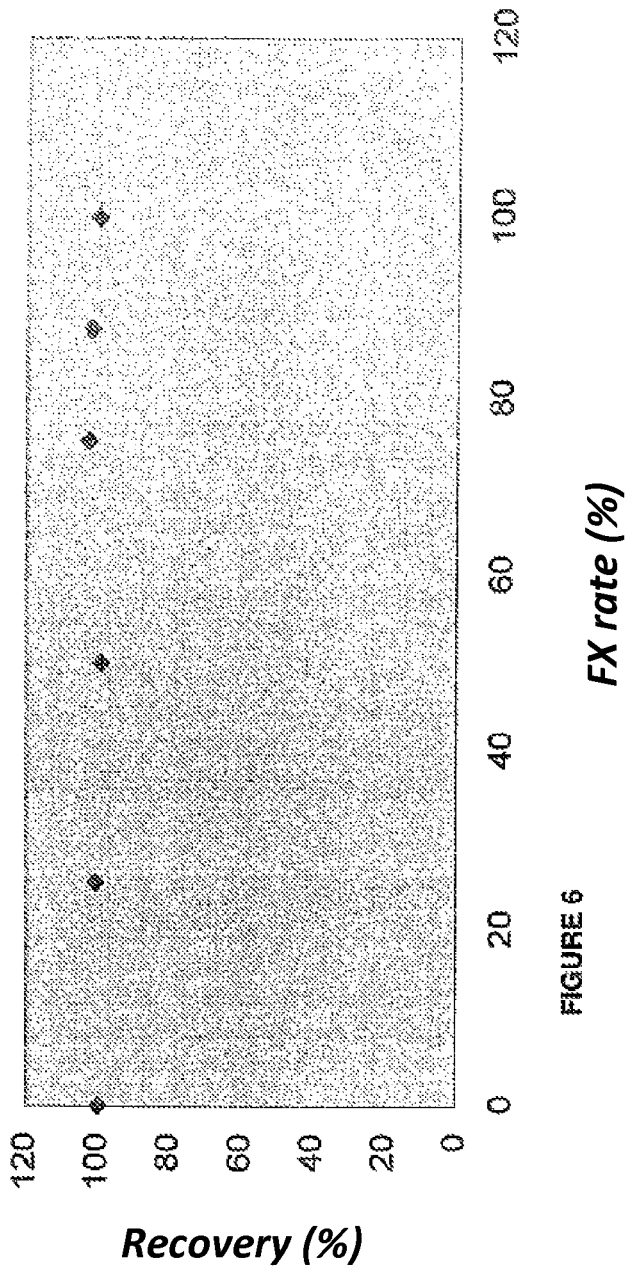

The results (FIG. 6 and Table 4) show, with recovery rates ≥99%, that the factor X rate in the sample does not influence the value of the functional activity of TF.

TABLE 4

Sensitivity to factor X (1)

| | X rate, % | | | | | |
|---|---|---|---|---|---|---|
| | 0 | 25 | 50 | 75 | 87.5 | 100 |
| Theoretical rate TF (pM) | 45.57 | 44.86 | 44.16 | 43.45 | 43.47 | 42.76 |
| Measured rate TF (pM) | 45.57 | 45.10 | 43.82 | 44.63 | 44.41 | 42.76 |
| Recovery % | 100 | 101 | 99 | 103 | 102 | 100 |

Sensitivity carried out from a deficient X and from a tissue factor-enriched pool.
0: def X-TF
25-87.5%: TF-pool/def X-TF
100%: TF-pool Plasmas enriched in TF containing a predetermined variable concentration of TFPI were assayed using the method described above.

They were:
plasma deficient in TFPI (0% column);
plasma from a pool rendered more or less deficient in TFPI (25-87.5% columns);
plasma from a normal pool (100% column).

Figure 7:
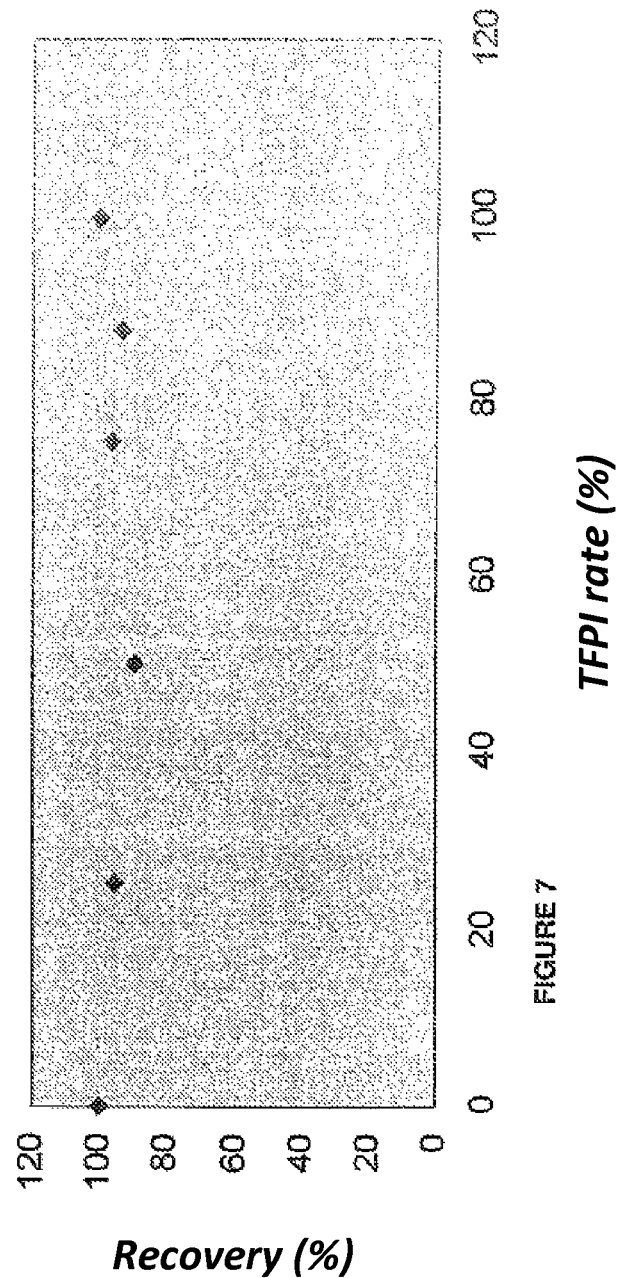

The results (FIG. 7 and Table 5) show, with recovery rates ≥93%, that the TFPI rate in the sample does not influence the value of the functional activity of TF.

TABLE 5

Sensitivity to TFPI (1)

| | TFPI rate, % | | | | | |
|---|---|---|---|---|---|---|
| | 0 | 25 | 50 | 75 | 87.5 | 100 |
| Theoretical rate TF (pM) | 48.25 | 46.86 | 45.50 | 44.13 | 43.44 | 42.76 |
| Measured rate TF (pM) | 48.25 | 44.86 | 40.77 | 42.54 | 40.55 | 42.76 |
| Recovery % | 100 | 96 | 90 | 96 | 93 | 100 |

Figure 8:
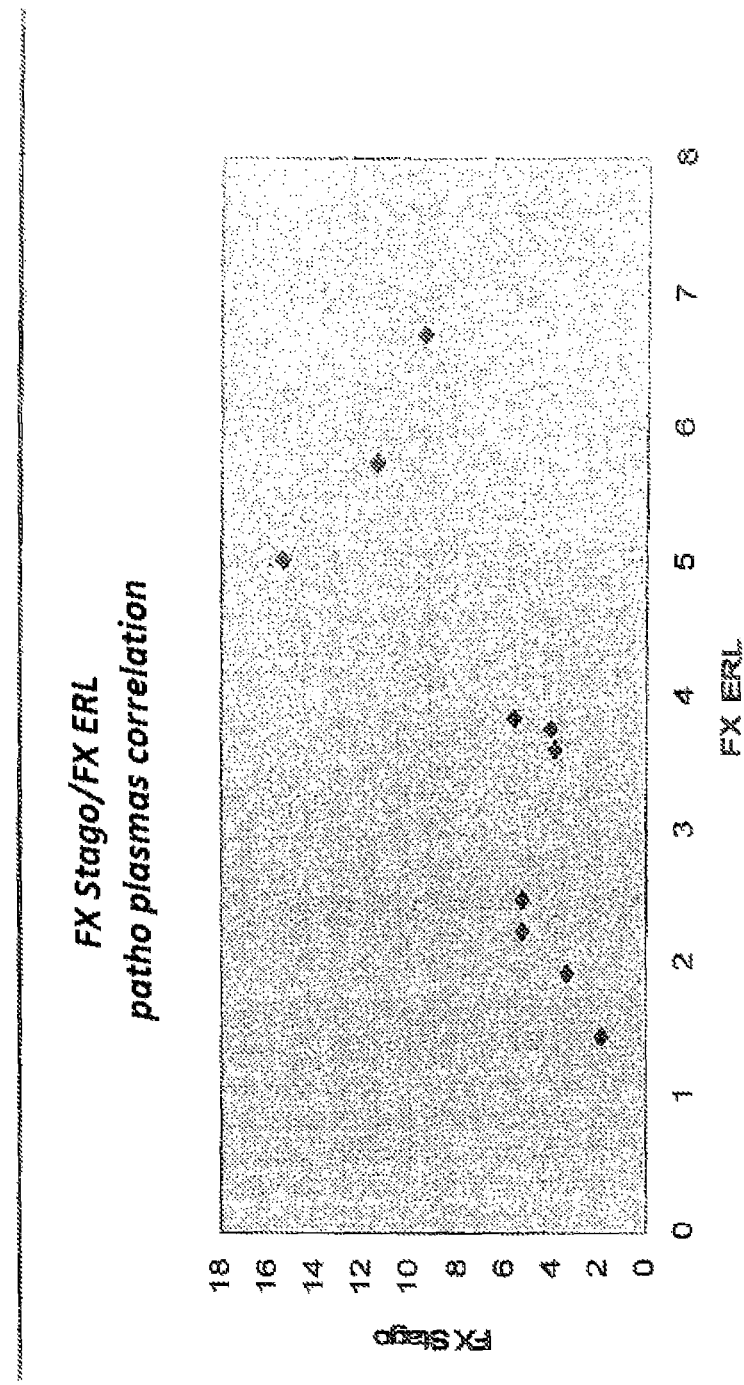
Figure 9:
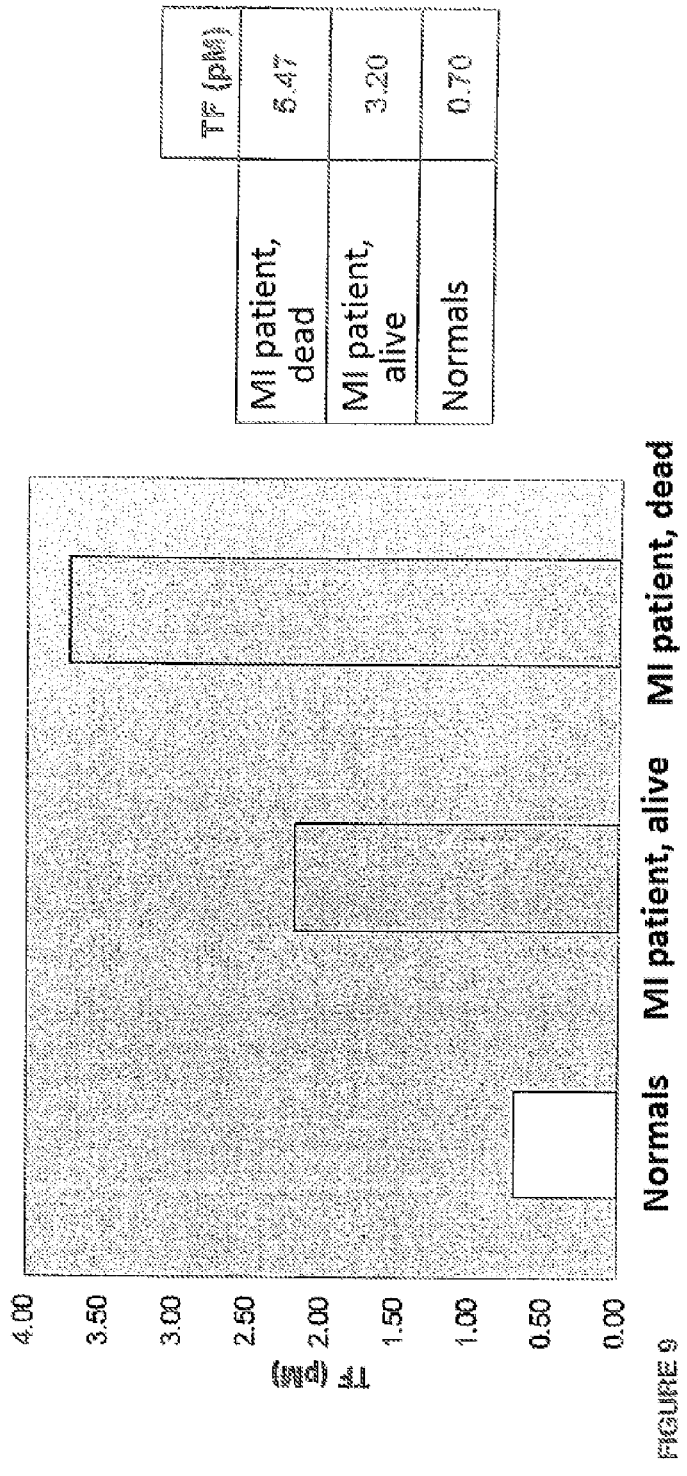

Sensitivity carried out from a deficient TFPI and from a tissue factor-enriched pool.
0: def TFPI-TF
25-87.5%: TF-pool/def TFPI-TF
100%: TF-pool As examples, in various pathologies,
the measurement of TF activity was carried out on a group of subjects who had no pathology and on the day of admission for a related group of patients suffering from myocardial infarction (MI), said group being divided into subjects with a good prognosis and patients who died in the days following the infarction (MI DCD); the TF rates were significantly higher in the MI patients than in the normal subjects, and substantially higher in those patients who died (FIG. 9);

circulating TF activity was also assayed in other thrombotic pathologies such as cancers, miscarriages: 3.65±1.35 to 3.92±1.29 depending on the stage at which the fetus was lost, thrombopenias induced by heparin (HIT): 6.33±2.10 pM; CIVDs: 2.81±1.52 pM, critical diabetes: 2.98±0.99 pM; and lupus: 1.95±0.82 pM or during pregnancy, in particular during complications in pregnancy such as preeclampsia: 3.58±1.34 pM compared with 1.98±1.35 pM during normal pregnancy; all of these determinations show a significant increase in the TF activity (FIG. 10);

measurement of repeatability:

The repeatability of the measurements was tested and produced the following values:

| | HIT | |
|---|---|---|
| | OD | pM |
| Mean | 0.186 | 16.19 |
| Min | 0.18 | 15.54 |
| MXa | 0.2 | 17.72 |
| Standard deviation | 0.005 | 0.528 |
| CV | 2.62 | 3.26 | correlating the measurements of factor X (ERL and Stago) on pathological plasmas produced the following results, illustrated in FIG. 8:

| | X ERL – X Stago correlation (1) | | | |
|---|---|---|---|---|
| | FX, ERL | | FX, Stago | |
| | OD | pM | OD | pM |
| Patho 1 | 0.088 | 2.85 | 0.074 | 4.91 |
| Patho 2 | 0.092 | 3.30 | 0.085 | 7.73 |
| Patho 3 | 0.127 | 7.39 | 0.143 | 22.6 |
| Patho 4 | 0.109 | 5.29 | 0.077 | 5.67 |
| Patho 5 | 0.095 | 3.66 | 0.085 | 7.73 |
| Patho 6 | 0.136 | 8.45 | 0.12 | 16.73 |
| Patho 7 | 0.112 | 5.64 | 0.087 | 8.25 |
| Patho 8 | 0.082 | 2.14 | 0.066 | 2.85 |
| Patho 9 | 0.111 | 5.53 | 0.078 | 5.94 |
| Patho 10 | 0.148 | 9.85 | 0.109 | 13.91 | the rate (in pM) of tissue factor from American Diagnostic was measured in accordance with the invention.

The results were read over a range produced from Neo-R Stago (single test) based on a concentration of TF of 6.2 nM in the Neo-R flask after reconstitution.

| | OD | pM |
|---|---|---|
| Pool + TF A.D. 30 pM | 0.259 | 23 |
| Pool + TF A.D. 15 pM | 0.175 | 13 |
| Pool + TF A.D. 7.5 pM | 0.113 | 5.9 |
| Pool + TF A.D. 3.75 pM | 0.089 | 3.0 |
| Pool + TF A.D. 1.88 pM | 0.073 | 1.1 |

BIBLIOGRAPHY

1. Valéry Daubie, Roland Pochet, Sophie Houard and Pierre Philippart. Tissue factor: a mini-review. J. Tissue Eng Regen Med. 2007; 1: 161-169.
2. Rüdiger Gerlach, Timm Scheuer, Martina Böhm, Jürgen Beck, Alina Woszczyk, Andreas Raabe, Inge Scharrer and Volker Seifert. Increased levels of plasma tissue factor pathway inhibitor in patients with glioblastoma and intracerebral metastases. Neurological Research, 2003; Vol 25, 335-338.
3. Anat Aharon, Benjamin Brenner, Tamar Katz, Yohei Miyagi, Naomi Lanir. Tissue factor and tissue factor pathway inhibitor levels in trophoblast cells: implications for placental hemostasis. Thromb. Haemost. 2004; 92: 776-86.
4. Nigel Mackman. Role of tissue factor in hemostasis and thrombosis. Blood cells Molecules and Diseases 2006; 36: 104-107.
5. Valéry Daubie, Roland Pochet, Sophie Houard, Pierre Philippart. Tissue factor: a mini-review J Tissue Eng Regen Med 2007; 1: 161-169.
6. Rachel Tilley, Nigel Mackman. Tissue factor in hemostasis and thrombosis. Semin Thromb and Hemost 2006; 31: 5-10.
7. Bjarne Osterud, Eirik Bjorklid. Sources of tissue factor. Semin Thromb and Hemost 2006; 32: 11-23.
8. Arthur J. Chu. Tissue factor mediates inflammation. Archives of Biochem and Biophy 2005; 440: 123-132.
9. Janusz Rak, Chloe Milson, Linda May, Petr Klement, Joanne Yu. Tissue factor in cancer and angiogenesis: The molecular link between genetic tumor progression, tumor neovascularization, and cancer coagulopathy. Semin Thromb and Hemost 2006; 32: 54-70.
10. Pierre-François Laterre, Xavier Wittebole, Christine Collienne. Pharmacological inhibition of tissue factor. Semin Thromb and Hemost 2006; 32: 71-76.

The invention claimed is:

1. A method for in vitro assay of the activity of circulating tissue factor (cTF) in a biological sample originating from the prior sampling of a patient, wherein the generation of activated factor X (Xa) is measured in a reaction medium comprising the tested biological sample, an excess of factor VII and of factor X, calcium ions, a fibrin polymerization inhibitor and a TFPI (Tissue Factor Pathway Inhibitor) activity inhibitor.

2. A method for the in vitro measurement of circulating tissue factor activity as claimed in claim 1, characterized in that the biological sample is a sample of blood or a derivative, especially a plasma sample.

3. A method as claimed in claim 1, characterized in that the generation of factor Xa in the reaction medium is determined by measuring the hydrolysis activity of said factor on a specific substrate.

4. A method as claimed in claim 3, characterized in that the specific substrate is an enzymatic substrate.

5. A method as claimed in claim 3, characterized in that the amidolytic activity of activated factor X (FXa) is assayed using a chromogenic or fluorometric substrate.

6. A method as claimed in claim 5, characterized in that the liberation of para-nitroaniline by the synthetic chromogenic substrate CBS 5244 is measured.

7. A method as claimed in claim 1, characterized in that the reaction medium comprises plasma diluted in an appropriate buffer, for example an Owren Koller buffer.

8. A method as claimed in claim 7, characterized in that the plasma is diluted in a dilution range of 1/2 to 1/20, for example 1/2 to 1/4; in particular, the plasma is diluted by 1/3.

9. A method as claimed in claim 1, characterized in that the fibrin polymerization inhibitor is a polypeptide inhibitor, for example H-GlyProArgPro-OH.AcOH (GPRP.AcOH) or is an anti-fibrinogen antibody.

10. A method as claimed in claim 1, characterized in that the calcium ions necessary for the initiation of coagulation are supplied in the form of $CaCl_2$.

11. A method as claimed in claim 1, characterized in that the inhibitor of the activity of TFPI on the circulating tissue factor is constituted by anti-TFPI antibody or functional antibody fragments binding the TFPI that are capable of inhibiting the activity of TFPI on circulating tissue factor.

12. A method as claimed in claim 11, wherein the TFPI inhibitor is a monoclonal T4E2 antibody or a functional fragment of said antibody.

13. A method as claimed in claim 2, comprising the steps of:
  a) bringing a plasma sample into contact with a reagent 1 comprising a fibrin polymerization inhibitor, an inhibitor of the activity of TFPI on cTF and, if appropriate, a dilution buffer;
  b) incubating the reaction medium constituted in step a) with a reagent 2 comprising factor X in excess, factor VII in excess and calcium ions in solution, in order to produce activated factor X (FXa);
  c) after incubation, bringing the reaction medium constituted in step b) into contact with an enzymatic substrate for activated factor X (FXa);
  d) detecting the transformation of the factor Xa substrate.

14. A method as claimed in claim 12, characterized in that the reagent 1 also comprises a heparin inhibitor, for example polybrene.

15. A method as claimed in claim 13, characterized in that the plasma sample is diluted by 1/3, in an Owren Koller buffer supplemented with 1.2 mg/L polybrene and 50 µg/L of anti-TFPI antibody.

16. A method as claimed in claim 13, characterized in that the quantitative measurement of the transformation of the enzymatic substrate for factor Xa is carried out by reading the optical density in a pre-determined window.

17. A method as claimed in claim 13, characterized in that the quantity of transformed factor Xa substrate is assayed by referring to a calibration curve.

18. A method as claimed in claim 13, characterized in that the reaction is carried out under the following conditions:
  for step a), the plasma sample diluted by 1/3 in an Owren Koller buffer is brought into contact with 50 µg/L of anti-TFPI antibody and 1.2 mg/L of polybrene and a fibrin polymerization inhibitor designated GPRP.AcOH in a concentration of 10 g/L;
  for step b), 25 µl of factor X in a proportion of 80 PEU/mg/mL, 25 µl of factor VII in a proportion of 137 PEU/mg/mL and 50 µl of a 25 mM $CaCl_2$ solution are added to 50 µl of the mixture of step a), and the reaction mixture obtained is incubated at 37° C. for 500 seconds;
  for step c), 100 µl of a solution of the enzymatic substrate for activated factor X is added and the quantity of transformed enzymatic substrate is determined by optical density reading in a reading window of 6 to 600 s, at a wavelength of 405 nm.

19. A method as claimed in claim 1, characterized in that it further comprises assaying an internal control.

20. A method as claimed in claim 1, characterized in that the optical density values obtained are compared with those of a calibration curve prepared using a pool of normal plasma enriched in tissue factor or using a NaCl—$CaCl_2$ solution enriched in tissue factor.

21. A method for the in vitro detection of a coagulation anomaly, comprising measuring the activity of circulating tissue factor as claimed in claim 1.

22. A method as claimed in claim 21, comprising comparing the measured circulating tissue factor activity with a normal value for said activity.

23. A method as claimed in claim 22, wherein the normal value is obtained after assaying the circulating tissue factor activity in a pool of normal plasma samples.

24. A method as claimed in claim 22, wherein the normal value is established from values for the activity of the circulating tissue factor measured on individually assayed normal plasma samples.

25. A method as claimed in claim 21, for the detection of an increase in the rate of circulating tissue factor associated with a risk of thrombosis or with a thrombosis, in particular with the symptoms of acute myocardial infarction (AMI), acute coronary syndrome, disseminated intravascular coagulation (DIVC), diabetes, preeclampsia, miscarriage, thrombosis, sepsis, inflammation or cancer.

* * * * *

UNITED STATES PATENT AND TRADEMARK OFFICE
CERTIFICATE OF CORRECTION

PATENT NO.       : 8,647,833 B2
APPLICATION NO. : 13/054578
DATED            : February 11, 2014
INVENTOR(S)      : Van Dreden et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 534 days.

Signed and Sealed this

Twenty-ninth Day of September, 2015

Michelle K. Lee
*Director of the United States Patent and Trademark Office*